United States Patent [19]

Thiele et al.

[11] 4,275,068
[45] Jun. 23, 1981

[54] LIPID LOWERING ALKYLENE GLYCOLS AND ESTER DERIVATIVES THEREOF

[75] Inventors: Kurt Thiele; Quazi Ahmed; Ulrich Jahn, all of Zofingen; Rudolf Adrian, Vordemwald, all of Switzerland

[73] Assignee: Siegfried AG, Zofingen, Switzerland

[21] Appl. No.: 48,536

[22] Filed: Apr. 23, 1979

[30] Foreign Application Priority Data

Aug. 29, 1977 [CH] Switzerland ............... 010498/77
Aug. 28, 1978 [WO] PCT Int'l Appl. ............... PCT/CH78/00015

[51] Int. Cl.³ ............... C07D 213/80; C07C 69/90; A61K 31/455; A61K 31/60
[52] U.S. Cl. ............... 424/266; 424/308; 424/311; 424/312; 424/340; 546/318; 560/107; 560/255; 560/108; 568/641
[58] Field of Search ............... 546/318; 560/108, 107, 560/255; 568/641; 424/266, 308, 311, 312, 340; 260/410.5

[56] References Cited

U.S. PATENT DOCUMENTS 3,969,419  7/1976  Engel et al. ............... 546/318
4,042,594  8/1977  Irikura ............... 546/318

FOREIGN PATENT DOCUMENTS 2502154  7/1975  Fed. Rep. of Germany ............... 568/641

OTHER PUBLICATIONS

Thummler et al., Chem. Abstracts, vol. 54, p. 25789 g-h 1960.

*Primary Examiner*—Alan L. Rotman
*Attorney, Agent, or Firm*—Werner W. Kleeman

[57] ABSTRACT

Novel alkylene glycol derivatives of the formula (1)

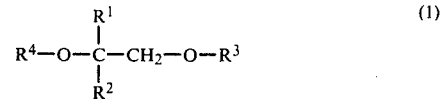

in which $R^1$ is the hydrogen atom, an alkyl group having 1-4 C-atoms or an aryl group, $R^2$ is the hydrogen atom or an alkyl group having 1-4 C-atoms, $R^3$ is the hydrogen atom or a group of the formula

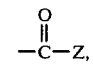

in which Z is an alkyl residue, an optionally substituted aryl residue or a heterocyclic residue and $R^4$ is a residue of the formula

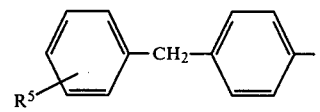

in which $R^5$ is the hydrogen atom or chlorine atom, or the methyl group, exhibit an advantageous activity in regard of lowering the cholesterol and triglyceride level in the blood. Production of the novel derivatives by reduction of the corresponding acids, or by reacting a phenol of the formula

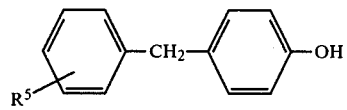

and an alcohol of the formula

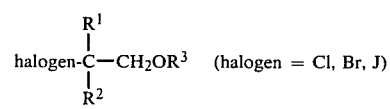

optionally with subsequent esterification, is described.

19 Claims, No Drawings

LIPID LOWERING ALKYLENE GLYCOLS AND ESTER DERIVATIVES THEREOF

TECHNICAL FIELD OF INVENTION

The invention relates to pharmacologically useful compounds having biological activity, to processes for producing such compounds and to pharmacological compositions containing such compounds.

PRIOR ART

Chemical agents for lowering unduly high cholesterol and triglyceride levels in the blood are known. An important group of such agents includes, as active ingredient, compounds of the formula (10)

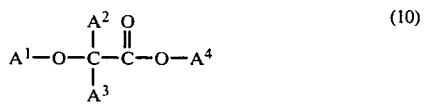

in which $A^1$ is an optionally substituted aryl residue, $A^2$ and $A^3$ are hydrogen or alkyl and $A^4$ is hydrogen or an organic residue. Compounds of the formula (10) in which $A^1$ is an optionally substituted phenyl or naphthyl residue are described inter alia in U.S. Pat. No. 3,262,850 as cholesterol-lowering agents among which the compound termed clofibric acid ($A^1$=p-chlorophenyl, $A^2$=$A^3$=methyl, $A^4$=H) and its ethyl ester ($A^4$=$C_2H_5$), the so-called clofibrate, respectively, have become of considerable clinical importance.

Further encompassed by the group of substances defined by formula (10) and known to have cholesterol-lowering properties are the compounds disclosed in the published German (Federal Republic) Patent application No. 2,356,655 ($A^1$=p-chlorobenzyl phenyl, p-chlorobenzyloxy phenyl and the like, $A^2$=$A^3$=methyl, $A^4$=H, alkyl or N,N-dialkylamino alkylene) and the compounds disclosed in the published German (Federal Republic) patent application No. 2,461,069 including specific variations with respect to groups $A^1$ to $A^4$, optionally using a sulphur link to group $A^1$ instead of an oxygen link.

In any case, a characteristic feature of the structure of the known cholesterol-lowering compounds of formula (10) is the 2-oxycarboxylic structure, or the 2-thiocarboxylic structure, respectively, and it was to be expected therefore that such carboxylic structure was essential for the lipid-lowering activity of the known compounds.

This invention aims at novel lipid-lowering compounds, at processes for producing such compounds, and at pharmacological compositions containing the novel lipid-lowering compounds.

INVENTION

Surprisingly, it was found that novel alkylene glycols of the formula (1)

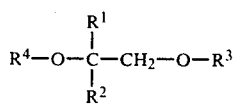

have an improved cholesterol-lowering effect, compared with clofibrate, even then when $R^3$ in formula (1) is hydrogen and when neither $R^1$ nor $R^2$ comprises a carbonyl group in α-position to the oxygen link, that is, when the 2-oxycarbonyl structure is lacking. On the other hand, the presence of a free hydroxy group (i.e. $R^3$=H) apparently is not essential for the cholesterol-lowering, or lipid-lowering effect, respectively, as esters of the formula (1) alcohols with organic acids exhibit lipid-lowering effects.

Thus, the invention resides in novel compounds of the above defined formula (1) in which the symbols $R^1$ to $R^4$ have the following significance:

$R^1$ is hydrogen, $C_1$-$C_4$ alkyl having a straight or branched chain, or aryl, such as benzyl.

$R^2$ is hydrogen or $C_1$-$C_4$ alkyl having a straight or branched chain.

In a preferred group of compounds of formula (1) $R^1$ is unlike $R^2$, particularly when both $R^1$ and $R^2$ are different lower alkyl groups, e.g. methyl/ethyl or methyl/propyl.

$R^3$ is, as noted, either the hydrogen atom or the residue of an organic acid required to form an ester, i.e. the group

in which Z generally is an alkyl residue, e.g. $C_1$-$C_{10}$ alkyl, or an optionally substituted aryl residue, e.g. the o-acetyloxy phenyl residue, or a heterocyclic residue, e.g. the 3-pyridinyl residue.

$R^4$ signifies a residue of the formula

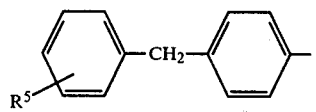

in which $R^5$ is hydrogen, chlorine or methyl. According to a preferred embodiment, $R^5$ stands for one of the substituents mentioned, notably chlorine, in p-position to the methylene link between the two benzene nuclei.

The novel compounds (1) can be obtained according to the invention from the corresponding acids or esters, respectively, of formula (2)

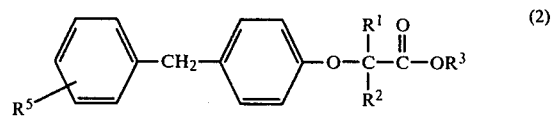

in which $R^1$ to $R^5$ have the significance given above, by reduction, preferably with lithium aluminum hydride in an organic solvent that is inert in the reaction. The acids of formula (2) are either known per se and can be obtained by the methods described in the above mentioned publications, or in analogous manner.

The novel compounds can also be obtained, according to the invention, from a phenol of the formula

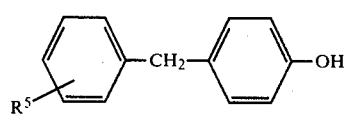

and an alcohol of the formula

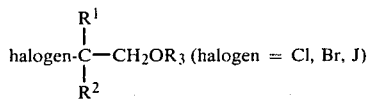

Activity values of compounds (1) and pharmacological compositions containing such compounds will be discussed below.

The following examples illustrate production of the novel compounds (1). Percents are by weight. The results of elemental analysis of the novel compounds are summarized in Table I below.

EXAMPLE 1

2-[4-(4'-chlorobenzyl)-phenoxy]-ethanol of the formula

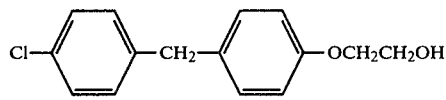

To a solution of 15.2 g (0.05 mol) of the ethyl ester of 2-[4-(4'-chlorobenzyl)-phenoxy]-acetic acid in 30 ml of dry diethyl ether there was added slowly a mixture of 1.9 g (0.05 mol) lithium aluminum hydride and 70 ml of dry diethyl ether. The mixture was stirred and refluxed for a period of 90 minutes, cooled and admixed with aqueous sodium hydroxide (10% NaOH in water). The precipitated salt was removed by filtration and the separated ether layer was evaporated after drying with magnesium sulfate. Crude target product in a yield of 12.9 g was obtained and recrystallized from dichloromethane/n-hexane to yield 10.59 g of pure target product, m.p. 64°–66° C.

EXAMPLE 2

2-methyl-2-[4-(4'-chlorobenzyl)-phenoxy]-butanol of the formula

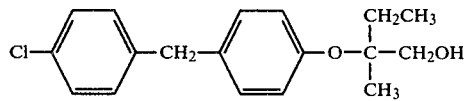

To a stirred slurry of 1.9 g (0.05 mol) of lithium aluminum hydride in 50 ml of dry diethyl ether there was added slowly a solution of 17.39 g (0.05 mol) of the ethyl ester of 2-methyl-2-[4-(4'-chlorobenzyl)-phenoxy]-butyric acid in 40 ml of dry diethyl ether. The mixture was stirred for 90 minutes and then decomposed with a 10% sodium hydroxide solution in water. The organic layer was separated, dried with magnesium sulfate and concentrated at reduced pressure to yield 15 g of an oily crude product that was distilled to yield 13 g of target product as a single liquid fraction, b.p. 193°–196° C./0.001 mm Hg.

EXAMPLE 3

2-phenyl-2-[4-(4'-chlorobenzyl)-phenoxy]-ethanol of the formula

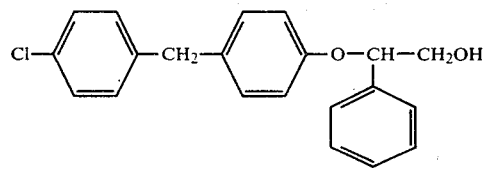

A solution of 53.3 g (0.14 mol) of the ethyl ester of 2-phenyl-2-[4-(4'-chlorobenzyl)-phenoxy]-acetic acid and 5.3 g (0.14 mol) of lithium aluminum hydride in 340 ml of dry diethyl ether was refluxed and stirred for 90 minutes. The reaction mixture was worked up as in Example 1 to yield 50 g of crude product that, after recrystallization from benzene, yielded 45 g of pure target product in the form of white crystals, m.p. 88°–89° C.

EXAMPLE 4

Ester of nicotinic acid and 2-[4-(4'-chlorobenzyl)-phenoxy]-ethanol of the formula

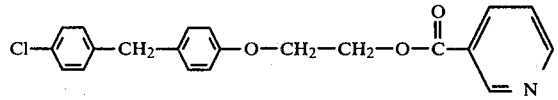

To a mixture of 8.9 g (0.05 mol) of nicotinoyl chloride hydrochloride and 10 ml of dry pyridine there was added slowly a solution of 13.2 g (0.05 mol) of 2-[4-(4'-chlorobenzyl)-phenoxy]-ethanol (the product of Example 1) in 20 ml of dry pyridine. The mixture was stirred for 24 hours at room temperature (20°–25° C.). Then, the pyridine was evaporated slowly under reduced pressure and the dried residue was taken up in a saturated aqueous sodium bicarbonate solution, the resulting mixture being extracted with trichloro methane. The organic phase was washed with water, dried over magnesium sulfate and evaporated to dryness. The residue was recrystallized from trichloro methane/n-hexane to yield 13 g of target product in the form of white crystals, m.p. 75°–78° C.

EXAMPLE 5

Hydrochloride of nicotinic acid ester of 2-methyl-2-[4-(4'-chlorobenzyl)-phenoxy]-butanol of the formula

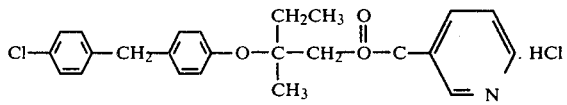

According to the procedure of Example 4, 12.6 g of 2-methyl-2-[4-(4'-chlorobenzyl)-phenoxy]-butanol (product of Example 2) were esterified with an equimolecular amount of the hydrochloride of nicotinoyl chloride in dry pyridine. The residue obtained after evaporating the pyridine is the base-form of the target ester in the form of an oily product yielding the corresponding hydrochloride by treatment with HCl/diethyl ether and providing, after recrystallization from methanol, 10.5 g of the pure target product in the form of colorless needles, m.p. 107° C.

EXAMPLE 6

Acetylsalicylic acid ester of 2-[4-(4'-chlorobenzyl)-phenoxy]-ethanol of the formula

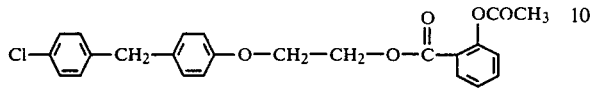

A solution of 13.2 g (0.05 mol) of 2-[4-(4'-chlorobenzyl)-phenoxy]-ethanol (product of Example 1) in 20 ml of 1,2-dichloro ethane was added to a mixture of 9.8 g (0.05 mol) of acetyl salicylic acid chloride and 12 ml of triethyl amine in 50 ml of 1,2-dichloro ethane. The reaction mixture was stirred for 20 hours at room temperature and then filtered. The filtrate was washed with water, dried over magnesium sulfate and the solvent removed under reduced pressure. The residue was recrystallized from dichloro methane/n-hexane to yield 10.5 g of the target product in the form of white crystals, m.p. 67°-69° C.

EXAMPLE 7

Acetylsalicylic acid ester of 2-methyl-2-[4-(4'-chlorobenzyl)phenoxy]-butanol of the formula

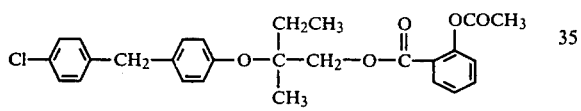

In accordance with the procedure of Example 6 a mixture of 7.9 g (0.04 mol) of acetylsalicylic acid chloride and 10 ml of triethyl amine in 50 ml of 1,2-dichloro ethane was reacted, while stirring, with a solution of 12.6 g (0.04 mol) of 2-methyl-2-[4-(4'-chlorobenzyl)-phenoxy]-butanol (product of Example 2) in 20 ml of dichloro ethane and worked up. The oily residue was distilled to yield 7.5 g of the target product in the form of a pale-yellow oil, b.p. 265°-270° C./0.05 mm Hg.

Further examples of inventive compounds (1) are given as follows:

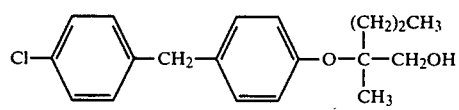

2-methyl-2-[4-(4'-chlorobenzyl)-phenoxy]-pentanol, b.p. 180°-183.5° C./0.01 mm Hg.

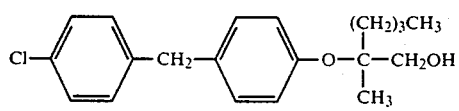

2-methyl-2-[4-(4'-chlorobenzyl)-phenoxy-]hexanol, b.p. 193°-196° C./0.001 mm Hg.

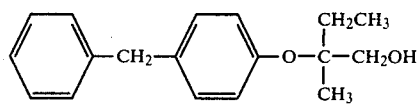

2-methyl-2-(4-benzylphenoxy)-butanol, b.p. 156°-157° C./0.001 mm Hg.

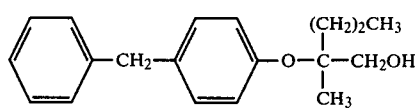

2-methyl-2-(4-benzylphenoxy)-pentanol, b.p. 165°-167° C./0.02 mm Hg.

TABLE I

| Example No. | Over-all formula | C | H | O | N | Cl |
|---|---|---|---|---|---|---|
| 1 | $C_{15}H_{15}ClO_2$ | | | | | |
| | calculated | 68.97 | 5.76 | 12.18 | | 13.49 |
| | found | 69.01 | 5.79 | 11.89 | | 13.57 |
| 2 | $C_{18}H_{21}ClO_2$ | | | | | |
| | calculated | 70.92 | 6.95 | 10.50 | | 11.63 |
| | found | 71.07 | 7.02 | 10.67 | | 11.63 |
| 3 | $C_{21}H_{19}ClO_2$ | | | | | |
| | calculated | 74.44 | 5.65 | | | 10.46 |
| | found | 74.88 | 5.79 | | | 10.67 |
| 4 | $C_{21}H_{18}ClNO_3$ | | | | | |
| | calculated | 68.52 | 5.00 | | 3.80 | |
| | found | 68.68 | 5.04 | | 3.50 | |
| 5 | $C_{24}H_{24}ClNO_3 \cdot HCl$ | | | | | |
| | calculated | 64.58 | 5.64 | | 3.14 | 15.89 |
| | found | 64.18 | 5.62 | | 2.77 | 15.92 |
| 6 | $C_{24}H_{21}ClO_5$ | | | | | |
| | calculated | 67.83 | 4.98 | 18.85 | | 8.34 |
| | found | 67.92 | 4.96 | 18.77 | | 8.54 |
| 7 | $CH_{27}H_{27}ClO_5$ | | | | | |
| | calculated | 67.44 | 5.83 | | | 7.60 |
| | found | 69.99 | 5.99 | | | 7.85 |

Toxicity values and activities of the above compounds (1) were investigated by animal tests in accordance with conventional methods as described, for example, in the above mentioned publications, and compared with the corresponding data of clofibrate, the well known cholesterol-lowering agent:

1. Toxicity

The $LD_{50}$ values of all compounds of Examples 1-7 on mice in mg of the active substance per kilogram of body weight are in the range of about 3000 and more and thus better, i.e. higher than in the case of clofibrate which has an $LD_{50}$ of 2180.

2. Cholesterol-Lowering

The $ED_{25}$ value, that is, the dosis in mg/kg body weight required for a 25% reduction of the cholesterol content of the blood, is 151 for clofibrate but better, i.e. lower, with all compounds (1) tested so far.

3. Triglyceride-Lowering

The $ED_{25}$ value, in this instance the dosis in mg/kg body weight required for a 25% reduction of the triglyceride content of the blood, is better, i.e. lower, with all compounds (1) tested so far than the corresponding activity value of 22 of clofibrate.

These data are summarized in the following Table II to facilitate review.

TABLE II

| Compound of Example No. | LD 50 Mice (mg/kg) | Cholesterol ED 25 (mg/kg) | Triglyceride ED 25 (mg/kg) |
| --- | --- | --- | --- |
| 1 | 3000 | 80 | <50 |
| 2 | 2960 | 80 | 14 |
| 3 | >3000 | >100 | |
| 4 | >3000 | 41 | 70 |
| 5 | >3000 | 30 | 40 |
| 6 | >3000 | 70 | >100 |
| Comparison Clofibrate: | 2180 | 151 | 222 |

The compounds (1) according to the invention can be used clinically substantially in the manner known for clofibrate, and employed for pharmaceutical compositions according to the invention, respectively.

To this end, compounds (1) can be formulated, singly or in mixtures with each other, if required in combination with other therapeutically active substances, in a manner known per se with conventional pharmacologically acceptable liquid or solid carriers and formulating adjuvants so as to yield liquid, semi-solid or solid compositions, notably for oral administration, e.g. as described in U.S. Pat. No. 3,262,850.

As an example of dosage units for medical treatment of unduly elevated cholesterol and triglyceride levels in the blood, a range of from about 0.05 to 1 g of active component (1) in pharmaceutical compositions according to the invention is given. Daily doses in the range of from about 0.1 to 10 g of active component (1) per patient correspond with those suggested for clinical use of clofibrate.

We claim:

1. A pharmaceutical composition for lowering cholesterol and lipid content of blood in human beings comprising an effective amount of active lipid lowering alkylene glycol derivatives of the formula (1)

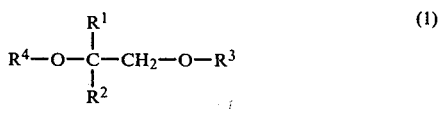

in which
  $R^1$ is the hydrogen atom, an alkyl group having 1–4 C-atoms or benzyl,
  $R^2$ is the hydrogen atom or an alkyl group having 1–4 C-atoms,
  $R^3$ is the hydrogen atom or a group of the formula

in which Z is an alkyl having 1 to 10 C-atoms, O-acetyloxyphenyl, or 3-pyridinyl and
  $R^4$ is a residue of the formula

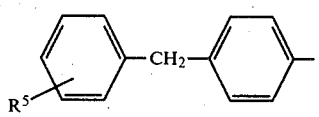

in which $R^5$ is the hydrogen or chlorine atom or the methyl group.

2. The pharmaceutical composition according to claim 1, wherein $R^5$ is the chlorine atom in p-position to the methylene link.

3. The pharmaceutical composition according to claim 2, wherein $R^1$ and $R^2$ each signify the hydrogen atom.

4. The pharmaceutical composition according to claim 2, wherein $R^1$ and $R^2$ represent different alkyl groups of from 1 to 4 carbon atoms each.

5. The pharmaceutical composition according to claims 2 or 4 wherein $R^3$ represents the acetyloxy benzoyl residue.

6. The pharmaceutical composition according to claims 2 or 4 wherein $R^3$ represents the nicotinoyl residue.

7. 2-[4-(4'-chlorobenzyl)-phenoxy]-alkanols in which the alkanol moiety includes from 1 to 4 C-atoms and esters thereof with pharmaceutically acceptable carboxylic acids.

8. A pharmaceutical composition according to claim 1 including pharmaceutically acceptable carrier.

9. A method of treating high blood levels of cholesterol and/or triglyceride in humans comprising the step of introducing into the blood a predetermined effective amount of the active compound of claim 1 or claim 2 and a pharmaceutically acceptable carrier.

10. The method according to claim 9 wherein the daily dosage of Formula 1 ranges from about 0.1 g to 10 g.

11. The method according to claim 9 wherein the dosage units of Formula 1 ranges from about 0.05 g to 1 g.

12. The pharmaceutical composition according to claim 2 wherein one of $R^1$, $R^2$ is methyl; the other of $R^1$, $R^2$ is ethyl.

13. The pharmaceutical composition according to claim 2 wherein one of $R^1$, $R^2$ is hydrogen; the other of $R^1$, $R^2$ is $C_1$-$C_4$ alkyl.

14. A compound of the Formula (1)

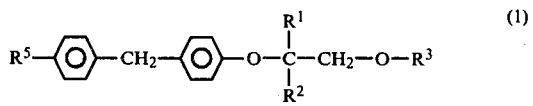

wherein $R^1$ is selected from the group consisting of hydrogen and alkyl groups having from 1 to 4 carbon atoms; $R^2$ is selected from the group consisting of hydrogen and alkyl groups having from 1 to 4 carbon atoms; $R^3$ is selected from the group consisting of hydrogen and acyl groups of the formula

wherein Z is selected from the group consisting of alkyl groups having from 1 to 10 carbon atoms, o-acetyloxy phenyl and pyridinyl; and $R^5$ is selected from the group consisting of hydrogen and chlorine with the proviso that $R^5$ is chlorine when $R^3$ is hydrogen.

15. The compound of claim 14 wherein $R^5$ is chlorine.

16. The compound of claim 14 wherein both $R^1$ and $R^2$ are hydrogen.

17. The compound of claim 14 wherein $R^1$ is selected from the group consisting of hydrogen and a first alkyl group having from 1 to 4 carbon atoms; and $R^2$ is selected from the group consisting of hydrogen and a second alkyl group having from 1 to 4 carbon atoms, said first alkyl group being different from said second alkyl group when both $R^1$ and $R^2$ are alkyl.

18. The compound of claim 14 wherein one of said $R^1$ and $R^2$ is methyl while the other is ethyl.

19. The compound of claim 7 wherein the organic acid is selected from the group consisting of nicotinic acid and acetyl salicyclic acid.

* * * * *